United States Patent [19]

Slemon

[11] Patent Number: 5,371,240
[45] Date of Patent: Dec. 6, 1994

[54] PROCESS FOR THE PREPARATION OF PURE THIOPHENE DERIVATIVES

[75] Inventor: Clarke Slemon, Willowdale, Canada

[73] Assignee: Torcan Chemical Ltd., Aurora, Canada

[21] Appl. No.: 983,316

[22] Filed: Nov. 30, 1992

[51] Int. Cl.$^5$ .................. C07D 333/22; C07D 333/28; C07D 333/38; C07D 333/08
[52] U.S. Cl. ........................................ 549/73; 549/70; 549/71; 549/80
[58] Field of Search ................. 549/73, 70, 71, 81, 549/80

[56] References Cited

U.S. PATENT DOCUMENTS 2,581,009  1/1952  Emerson et al. .................... 549/73
2,714,111  7/1955  Herman ............................. 549/70

OTHER PUBLICATIONS

J. March, "Advanced Organic Chemistry," p. 17 3rd ed., John Wiley & Sons, New York (1985).
Synthetic Communications, 11(1), 29–34 (1981) "Bromination of Some Heteroaromatic Acyl Compounds With Aqueous Bomine/Sodium Acetate".

Primary Examiner—Glennon H. Hollrah
Assistant Examiner—Deborah Lambkin
Attorney, Agent, or Firm—Ridout & Maybee

[57] ABSTRACT

3-substituted thiophene compounds contaminating the analogous 2-substituted thiophene compounds, e.g. 3-acetylthiophene contaminating 2-acetyl thiophene, are removed by a selective electrophilic substitution process, e.g. bromination, followed by fractional distillation. It has been found that electrophilic substitution as exemplified by bromination is highly selective towards the 3-substituted thiophenes, yielding compounds of significantly higher molecular weights for separation purposes, to give high purity 2-substituted thiophene compounds.

7 Claims, No Drawings

PROCESS FOR THE PREPARATION OF PURE THIOPHENE DERIVATIVES

FIELD OF THE INVENTION

This invention relates to processes for preparing substituted thiophenes, and more specifically, to processes for preparing substituted thiophenes in particularly pure form, useful as intermediates in the synthesis of various pharmaceuticals.

BACKGROUND OF THE INVENTION AND PRIOR ART

Thiophene compounds substituted at the 2-position, especially 2-acyl-substituted thiophenes such as 2-acetylthiophene, 2-thiophenecarboxylic acid and 2-thiophenecarbonyl chloride, are used as intermediates in the synthesis of pharmaceuticals. For example, 5-chloro-2,3-dihydro-2-oxo-3-(2-thienylcarbonyl)-1H-indole-1-carboxamide ("tenidap") involves, as one of its synthetic steps, the reaction of a 2-carbonyl-substituted thiophene such as 2-thiophenecarbonyl chloride with an appropriate indole compound. 2-Thiophenecarbonyl chloride is most simply prepared from 2-acetylthiophene first by the halo form reaction to produce 2-thiophenecarboxylic acid followed by transformation to the acid chloride using thionyl chloride or an equivalent reagent, thus:

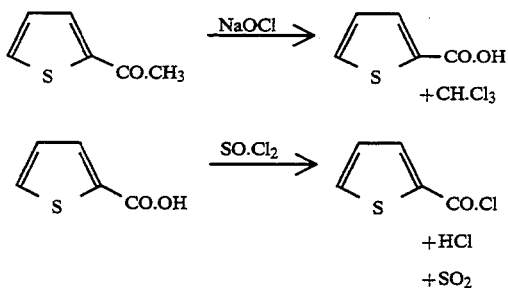

2-Acetylthiophene is normally prepared by Friedel-Crafts acetylation of thiophene with acetic acid or an activated form thereof such as acetic anhydride. The product is normally purified by distillation and it regularly contains from 1-2% of the 3-acetylthiophene as an impurity. This by-product cannot easily be removed, because the substances boil within a few degrees of each other. For most purposes, 2-acetylthiophene of 98-99% purity is adequate.

However, when 2-thiophenecarbonyl chloride is used in the synthesis of the drug tenidap, it has been found that even a low level of 3-thiophenecarbonyl chloride contaminating the 2-thiophenecarbonyl chloride in this synthesis leads to an unacceptable quality of the final product, requiring further purification. The final product is purified only with difficulty, and with attendant losses of expensive product.

The 2-thiophenecarboxylic acid and the 2-thiophenecarbonyl chloride produced from 2-acetylthiophene by the above reaction are still contaminated with the corresponding 3-substituted products. These impurities are so similar to the desired 2-substituted products that they cannot effectively be removed therefrom without suffering substantial losses of the desired product.

It is an object of the present invention to provide a novel process for preparing 2-substituted thiophenes essentially free from the corresponding 3-substituted thiophene impurities.

SUMMARY OF THE INVENTION

The present invention provides a process whereby 3-substituted thiophenes present as impurities in admixture with corresponding 2-substituted thiophenes are removed therefrom by selective electrophilic aromatic substitution of the 3-substituted thiophene, e.g. by bromination. It has been found that, using simple and inexpensive reaction conditions, 3-substituted thiophenes such as 3-acetyl thiophene can be selectively brominated, even when the 3-substituted compound constitutes only 0.1-2% of a mixture with its corresponding 2-substituted thiophene. This yields compounds of sufficiently different physical properties that the large excess of the desired 2-substituted thiophene can be readily separated, e.g. by fractional distillation, to yield essentially pure 2-substituted thiophene.

Whilst it is not intended that this invention should be limited to any particular theory or mode of operation, it is believed that the electronic configuration of the substituted thiophene compounds is responsible for this highly selective electrophilic attack with the electrophile. The sulfur in the thiophene ring controls the preferred position for electrophilic attack. It directs electrophiles to the carbons adjacent to sulfur, conventionally numbered 2 or 5. When either the 2 or 5 positions are substituted by a strongly electron withdrawing, resonance stabilizing group such as acyl, aldehydo, carboxyl or nitro, electrophilic substitution is:

(a) blocked in the position which the group itself occupies, and (b) severely retarded at the other preferred position next to sulfur.

This reduction in electron density at the unsubstituted 2 or 5 position can be formally rationalized by the presence of a substantially contributing resonance structure such as A, B, C, or D:

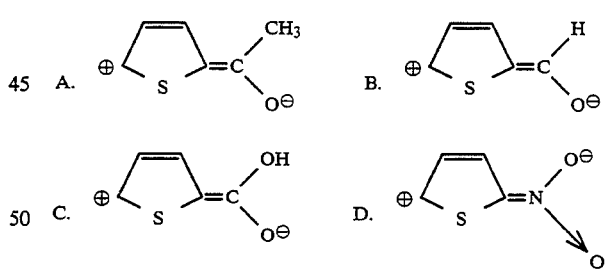

Indeed, substrates which are candidates for this technology can be identified by the presence of such a significant resonance contributor.

The result is that the presence of an electron-withdrawing resonance stabilizing functionality at either the 2 or 5 positions of a thiophene compound substantially reduces the reactivity of that derivative to electrophilic attack. In contrast, the presence of the same functionality at the 3 or 4 positions, physically blocks neither of the more reactive 2 or 5 positions and substantially reduces the reactivity to electrophilic substitution only at the nearest of these positions; hence, there remains substantial electron density at one reactive position next to sulfur and so the overall reactivity of the derivative is not substantially affected. Consequently, thiophenes substituted by electron-withdrawing resonance-stabilizing groups at the 3 or 4 positions are generally orders of magnitude more reactive to electrophilic substitution than the corresponding 2 or 5 substituted thiophenes. The practical result is that the 3 or 4 substituted thiophenes, even when present as an impurity, at a level of as low as 0.2-2.0% by weight, in the corresponding 2 or 5 substituted thiophenes, still react competitively with appropriately chosen electrophiles under appropriately mild conditions.

Thus, according to an aspect of the present invention, there is provided a process for the separation a 3-substituted thiophene compound from a mixture thereof with an analogous 2- substituted thiophene compound in which the 2- substituted thiophene compound predominates, which comprises selective electrophilic substitution of the 3- substituted thiophene compound in the mixture to create a chemically modified 3- substituted thiophene compound of significantly different physical properties, and subsequent removal of the significantly different 3- substituted thiophene compound or a derivative thereof from the analogous 2- substituted thiophene compound or a derivative thereof from the analogous 2- substituted thiophene compound on the basis of the significant differentiation in physical properties.

DESCRIPTION OF THE PREFERRED EMBODIMENTS

The preferred electrophilic substituting agents are brominating reagents. Specific preferred examples of such are bromine, 1,3-dibromo-5,5-dimethylhydantoin, N-bromosuccinimide, N-bromocaprolactam, bromotrichloromethane, cupric bromide, 1,2-dibromotetrachloroethane, N-bromoacetamide, phenyltrimethylammonium perbromide, pyridinium bromide perbromide, pyrrolidone-2-hydrotribromide, 2,4,4,6-tetrabromo-2,5-cyclohexadieone, omegatribromoacetophenone, and the like.

Whatever the full theoretical explanation of the operation of the process, in this preferred embodiment where brominating reagents are used, the net result is a highly competitive bromination of the 3- substituted thiophene, to form a 5-bromo-thiophene compound, even when the 3- substituted thiophene is present only in an amount of 0.1-2% of the total mixture. The selectively brominated 3- substituted compound and the small amounts of brominated 2- substituted compound have a much higher molecular weight than the non-brominated 2- substituted analog, allowing for easy separation, e.g. by distillation. Alternatively, the crude mixture can be further reacted, and separation effected by distillation of derivative compounds, from those originally reacted with the brominating reagent.

Preferably, the substituents on the thiophene nucleus are acyl substituents, which appear to have the effect of enhancing the electronic configurations of the compounds in favour of even greater selectivity of electrophilic attack. Most preferred among the mixtures be separated is 2-acetylthiophene contaminated with 3-acetylthiophene impurity, this compound having direct utility in the synthesis of the pharmaceutical tenidap. Following the bromination step, the 2-acetylthiophene may be separated from the brominated 3-acetylthiophene by simple fractional distillation, since the boiling points of the two compounds are significantly different. Most preferably, the reaction mixture from the bromination step is subject to the haloform reaction followed by transformation to the acid chloride. Distillation to recover the 2-thiophenecarbonyl chloride from the reaction mixture is required in any event, so that separation of the 2-thiophenecarbonyl chloride from the brominated 3-substituted thiophene contaminants can be effected at this time, without requiring a further and separate distillation-separation step.

The conditions of the selective bromination reaction are simple and inexpensive. Reaction temperatures are suitably in the range −15° C. to 30° C., for a time up to 24 hours. A molar excess of bromine, in relation to the 3-substituted thiophene impurity, should be supplied by the brominating reagent, suitably a 2-10 fold excess.

The invention is further described for illustrative purposes in the following specific examples.

DETAILED DESCRIPTION OF THE MOST PREFERRED EMBODIMENTS

EXAMPLE 1

Selective Bromination with Bromine—Aqueous Sodium Acetate

A 9.78 gram sample of 2-acetylthiophene containing 3.7-4.0% 3-acetylthiophene was placed in a 100 ml round bottom flask equipped with a magnetic stirrer and thermometer. Sodium acetate (0.70 g) and 10 mL of water were added and the heterogeneous mixture vigorously stirred and cooled in an ice bath. Liquid bromine (1.37 g; 11 mole percent) was added all at once to the ice-cold mixture. For 1.5 hours, the yellow slurry was vigorously mixed at 0°−+5° C. The flask was then packed in ice and left stirring overnight slowly to warm to room temperature. In the morning the brown oil and the white aqueous phase were separated into layers and the oil washed with 10 ml of 1N sodium thiosulfate diluted with 10 mL of water. The layers were separated and the aqueous phase washed with 20 mL of methylene chloride which was added to the brown oil. The combined methylene chloride and brown oil were washed with 20 ml of water and the lower organic layer dried with magnesium sulfate. The organic layer was filtered to remove drying agent and vacuum evaporated to remove methylene chloride. Vacuum distillation of the brown oil through a vacuum jacketed Vigreux column, which had previously been demonstrated not to separate acetylthiophenes, produced a distillate which showed on analysis by GC and HPLC 0.41% and 0.42-0.45% 3-acetylthiophene. The starting material showed 3.84% and 3.7% 3-acetylthiophene by GC and HPLC analysis.

EXAMPLE 2

Selective Bromination with Bromine—Sodium Acetate

To 42.79 gm of crude acetylthiophene containing 1.6-1.7% 3-acetylthiophene stirred vigorously in a 500 ml round bottom flask and cooled to 3°-5° C. was added 3.04 gm of sodium acetate in 40 ml of water followed by 2.5 ml of liquid bromine in portions. The reaction is exothermic and the temperature rose to 9° C. The temperature was immediately cooled back to 3°-5° and the remaining bromine added cautiously. Over 6 hours the temperature gradually rose to 20° C. and the flask was left stirring overnight. The reaction produced a red lower layer and a clear white upper layer. Solid sodium thiosulfate (0.1 gm) was added and the layers mixed to dissolve the solid. The lower organic layer was separated and combined with 5 ml of toluene which was used to wash the water. Vacuum distillation at water aspirator vacuum gave a trace of toluene-water forerun followed by 33.95 gm bp @89°-94° C. fraction A, and 5.23 gm bp@95°-105° C. fraction B. Neither fraction A nor fraction B contained a detectable amount of 3-acetylthiophene where the quantifiable level is 0.25%. The difference in the boiling points of the fractions reflects different levels of bromoacetylthiophenes which pass over using this fractionation apparatus.

EXAMPLE 3

Selective Bromination with Dibromo—Dimethylhydantoin

In a 2000 mL three-necked round bottom flask equipped with a mechanical stirrer and thermometer was placed 401.5 g of commercial 2-acetylthiophene and 400 mL of tap water. The stirrer was started, mixing the immiscible liquids together vigorously. At an internal temperature of 15°-20° C. there was added by powder funnel 27.75 g of 1,3-dibromo-5,5-dimethylhydantoin into the stirred mixture. There was no exotherm. The mixture was a slurry with the pinkish solid still insoluble and dispersed into both phases. The reactor was closed and with continued vigorous stirring the temperature was raised to 20°-25° C. over 1 hour. The reaction was monitored closely for a possible exotherm to ensure that the temperature did not exceed 40° C. The reactor contents were stirred at between 20° and 27° C. for 5 hours. By this time a test for oxidant using moist, acidic starch iodide test paper was negative and the solid phase had completely dissolved. To the two phase mixture was added a solution of 3.9 g of sodium thiosulfate dissolved in 83 ml of water. The deep red colour went to an orange-brown upon stirring for ten to fifteen minutes at room temperature. Into the two phase mixture was added 100 mL of methylene chloride and stirring continued for 15 minutes; then the layers were allowed to separate. The lower layer was cut. The aqueous upper layer, which was white, was washed with 40 ml additional methylene chloride and the organic extracts combined. The combined organics were placed in a 1 liter flask under a Dean-Stark trap and heated with stirring in a 70° C. bath to azeotrope off water. About 4 ml was collected. The equipment was changed for downward distillation and the methylene chloride removed at a temperature of 35°-40° C. and not heating above 70° C.

EXAMPLE 4

Purified 2-Acetylthiophene

The turbid solution from Example 3 was placed into a 250 mL glass still pot with a magnetic stirring bar under a 10 centimeter high, vacuum-jacketed glass Vigreux column. The assembly had a thermometer in the Claisen neck just beneath the column and a second thermometer at the top of the column. The distillation of the main fraction was done at a pressure of about 10 mbar. Under vacuum with vigorous stirring in the still pot the oil bath temperature was gradually raised to 120°-130° C. first to remove the methylene chloride and then any forerun distilling below 90° C. was removed. The main fraction distilled as a water white or pale green liquid between 89° and 95° C. This fraction, 76-83 grams, represented about 76-83% of the input weight of 2-acetylthiophene. A higher boiling fraction could be forced over boiling between 95° and 105° C. which contained a larger proportion of 2-acetyl-5-bromothiophene and 3-acetyl-5-bromothiophene.

EXAMPLE 5

2-Thiophenecarboxylic Acid

In a one liter three-necked round bottom flask equipped with a magnetic stirrer, thermometer and addition funnel was placed 25.2 g of crude 2-acetylthiophene Example 3 and 25 ml of water. With vigorous stirring at 30° C., 580 g of concentrated 12% bleach was added in a stream while maintaining the internal temperature in the range 25°-40° C., preferably 30°-35° C. An ice-methanol bath was used for cooling during this very exothermic addition. The addition took 20-25 minutes. After the addition was complete, stirring was continued for one hour while the temperature was maintained at 30°-33° C. There was formed a small lower layer of the chloroform produced in the reaction and a large aqueous phase in which the sodium salt of the product was dissolved. The phases were allowed to separate. The lower layer was cut in a separatory funnel. To the aqueous phase 5 ml of methylene chloride was added, stirred and allowed to settle. This was cut and combined with the chloroform. Then 5 g sodium sulfite was added and stirred for ten minutes. The aqueous phase was stirred and the internal temperature adjusted to the range 0°-5° C. The solution was acidified by adding gradually 65 mL of concentrated hydrochloric acid to give a pH of 0.5-1.2. The white solid which precipitated was filtered on a Buchner and washed with 2×100 mL of water. The wet solid was used as is, in the next step. The wet weight of product was in the range 40-50 g.

EXAMPLE 6

Crude 2-Thiophenecarbonyl Chloride

Into a three-necked 2000 mL round bottom flask equipped with a mechanical tru-bore stirrer, a thermometer and a Dean-Stark trap and reflux condenser, was placed 450 ml of toluene, and 338.8 g of somewhat wet 2-thiophenecarboxylic acid from the previous Example, to produce a slurry. The vessel was cooled and the reactor heated to azeotrope out the water. The water was collected until the returning liquid was clear. One hundred mL of toluene was distilled out. At 65°-70° C. 0.06 g of N-methylpyrrolidinone was added. The Dean Stark trap was replaced with a reflux condenser which was cooled sufficiently to keep the thionyl chloride in the reactor even as gases were vigorously evolved. The reactor was connected to a sparger to trap evolving hydrogen chloride and sulfur dioxide gases. Into this stirred mixture at between 65°-70° C. was added gradually 422.8 g of thionyl chloride at such a rate that the temperature was controlled in the specified range and the evolution of gases did not cause too vigorous foaming. The temperature was maintained at 65°-70° C. for four (4) hours after completion. Starting at 65°-70° C. the residual thionyl chloride was removed by heating the mixture up to an internal temperature of 130° C. This forerun of thionyl chloride and toluene distilled between 75° and 130° C. The residue was cooled to 0°-5° C. and vacuum applied. Material was distilled until a reactor temperature of 100° C. was reached. The crude residual acid chloride was a brown liquid. The weight of crude product was between 320-340 grams.

EXAMPLE 7

2-Thiophenecarbonylchloride

A three-necked round bottom flask equipped with a thermometer, magnetic stirrer and uninsulated column filled with Raschig rings (reported five theoretical plates) topped with a Perkins triangle still head combination, was loaded with 165.8 g of crude acid chloride. The charge was washed in with 5 ml of toluene. With stirring, a vacuum of 7–8 mm mercury was gradually applied to the pot and column. A forerun of 1–10 ml distilled at a temperature of less than 50° C. at the stillhead and was removed. A main fraction of 92 ml (124.7 g) [purity 100%; no bromo impurity] was removed between 76°–78° C. The bath temperature was held at 140° C. The temperature at the base of the column was over 120° C. A second product fraction was removed boiling between 76°–78° C. This material weighed about 20 g[99.89%; 0.11% bromo impurity]. A third main fraction was removed boiling at 76°–78° C. weighing about 3.3 g [99.69%; 0.31% bromo impurity]. The still pot residue was about 7.5 g [45.5% bromo impurity]. The distillates were protected at all times from moisture with which they react vigorously. The first two fractions were combined, and together these gave 144.7 g. Based on crude oil this was an 87% mass yield.

I claim:

1. A process for the separation of a 3-acyl substituent thiophene compound from a mixture thereof with an analogous 2-acyl substituted thiophene compound in which the 2-acyl substituted thiophene compound predominates, which comprises selective bromination of the 3-acyl substituted thiophene compound in the mixture to create a brominated 3-acyl substituted thiophene compound of significantly different physical properties, and subsequent removal of the brominated 3-acyl substituted thiophene compound or a derivative thereof from the 2-acyl substituted thiophene compound by fractional distillation.

2. The process of claim 1 wherein the selected bromination is accomplished using a brominating agent selected from the group consisting of bromine; 1,3-dibromo-5,5-dimethylhydantoin; N-bromo succinimide; N-bromocaprolactam; bromotrichloromethane; cupric bromide; 1,2-dibromotetrachloroethane; N-bromoacetamide; phenyltri-methylammonium perbromide; pyridinium bromide perbromide; pyrrolidone-2-hydrotribromide; 2,4,4,6-tetrabromo-2,5-cyclohexadienone; and omega tribromoacetophenone.

3. The process of claim 1 wherein the 2-substituted thiophene compound is 2-acetylthiophene and the 3-substituted thiophone compound is 3-acetylthiophene.

4. The process of claim 3 wherein reaction with the brominating agent takes place at a temperature of from −15° C. to 30° C.

5. The process of claim 4 wherein the amount of brominating agent used is sufficient to provide a twofold -tenfold molar excess of bromine over the 3-acetylthiophene.

6. The process of claim 3 wherein the steps of halo form reaction to convert the acetylthiophenes to the corresponding acids, and chlorination to convert the acids to acyl chlorides, are interposed between the reaction with the brominating agent and the separation on the basis of molecular weight differentiation.

7. The process of claim 6 wherein brominated 3-thiophenecarbonyl chloride is separated from 2-thiophenecarbonyl chloride by fractional distillation.

* * * * *